United States Patent [19]

Spiegelman

[11] 4,379,839
[45] Apr. 12, 1983

[54] METHOD FOR DETECTING CANCER

[75] Inventor: Sol Spiegelman, New York, N.Y.

[73] Assignee: The Trustees of Columbia University in the City of New York, New York, N.Y.

[21] Appl. No.: 126,166

[22] Filed: Feb. 29, 1980

Related U.S. Application Data

[63] Continuation of Ser. No. 872,855, Jan. 27, 1978, abandoned, which is a continuation-in-part of Ser. No. 799,810, May 23, 1977, abandoned.

[51] Int. Cl.³ .................. C12Q 1/70; G01N 33/54; G01N 33/56; G01N 33/60
[52] U.S. Cl. .................................. 435/5; 435/7; 424/1; 424/1.5
[58] Field of Search .............. 435/5, 7, 810; 424/1, 424/8, 12; 23/230 B

[56] References Cited

U.S. PATENT DOCUMENTS

| | | | |
|---|---|---|---|
| 3,755,086 | 8/1973 | Heimer | 435/6 |
| 3,798,131 | 3/1974 | Rounds et al. | 435/6 |
| 3,816,263 | 6/1974 | Rabin et al. | 435/19 |
| 3,852,415 | 12/1974 | Vandervoode | 424/1 |
| 3,859,430 | 1/1975 | Parikh et al. | 424/1 |
| 3,867,363 | 2/1975 | Hansen | 260/112 R |
| 3,988,115 | 10/1976 | Modabber | 424/12 X |
| 3,999,944 | 12/1976 | Grosser et al. | 424/12 X |
| 4,002,532 | 1/1977 | Weltman et al. | 424/12 X |
| 4,016,043 | 4/1977 | Schuurs et al. | 424/12 X |
| 4,043,757 | 8/1977 | Wagstaff | 424/12 X |
| 4,146,603 | 3/1979 | Davidson et al. | 424/1 |

FOREIGN PATENT DOCUMENTS 977681 11/1975 Canada .

OTHER PUBLICATIONS

Martin et al., Cancer Chemotherapy Reports (part 2) vol. 5, No. 1, pp. 89–103, (Dec. 1975).
Rainer et al., The Lancet, pp. 357–358, (1974).
Ritzi et al., Virology, vol. 75, pp. 188–197, (1976).
Ritzi et al., Proc. Natl. Acad. Sci., vol. 73, No. 11, pp. 4190–4194, (Nov. 1976).
Schlom et al., Am. J. Clin. Pathol., vol. 60, pp. 44–56, (Jul. 1973).
Ohno et al., Proc. Natl. Acad. Sci. U.S.A., vol. 74, pp. 764–768, (1977).
Schlom et al., Proc. Natl. Acad. Sci. U.S.A., vol. 68, No. 7, pp. 1613–1617, (1971).
Marcus et al., Virology, vol. 71, pp. 242–253, (1976).
Axel et al., Nature, vol. 235, pp. 32–36, (1972).
Undenfriend et al., Science, vol. 178, pp. 871–872, (1972).
Witkin et al., Proc. Natl. Acad. Sci. U.S.A., vol. 72, No. 10, pp. 4133–4136, (1975).
Nakane et al., J. Histochem. Cytochem., vol. 22, No. 12, pp. 1084–1091, (1974).

*Primary Examiner*—Lionel M. Shapiro
*Attorney, Agent, or Firm*—Stephen P. Gilbert

[57] ABSTRACT

The existence and status of cancers in humans can be detected by assaying for viral related proteins in plasma samples. Suitable viral related proteins include the enzyme RNA-dependent DNA polymerase (reverse transcriptase) or an extracellular tumor associated protein which is of viral origin. The aforesaid enzyme and tumor associated protein are immunologically cross-reactive with antibodies to Mason-Pfizer Monkey Virus (MPMV) and murine mammary tumor virus (MMTV) which thereby provide a convenient source of reagents for the instant method.

14 Claims, No Drawings

METHOD FOR DETECTING CANCER

The invention described herein was made in the course of work under a grant or award from the Department of Health, Education and Welfare.

This is a continuation of application Ser. No. 872,855, filed Jan. 27, 1978, which in turn is a continuation-in-part of application Ser. No. 799,810, filed May 23, 1977, both now abandoned.

BACKGROUND OF THE INVENTION

Studies with the murine mammary tumor model have established the feasibility of using plasma-concentrations of viral protein to assess the presence and status of a solid tumor. The viral protein utilized for such studies was a 52,000 dalton glycoprotein (gp 52) isolated from the murine mammary tumor virus (MMTV) using affinity chromatography. Availability of purified gp 52 by the aforesaid procedure allowed development of a radioimmunoassay to this protein sensitive to plasma levels down to 0.1 ng/100 μl. See in regard to the above Ritzi et al., Virology, 75, 188 (1976) and Ritzi et al., Proc. Natl. Acad. Sci. USA, 73, No. 11, 4190 (1976).

The relationship between the mammary tumors and the plasma levels of gp 52 were found to be as follows:

(a) tumor-bearing mice, male or female, showed markedly elevated (100–1000 ng/ml) levels of gp 52 as a free soluble protein in the plasma and the mean concentration increased with average tumor size;

(b) the presence of another malignancy (leukemia) did not result in any change of gp 52 levels in the plasma;

(c) mammary tumor tissue located by transplantation outside the mammary gland is also detected by high plasma gp 52 levels;

(d) low (2–10 ng/ml) plasma levels of gp 52 are found in tumor free mice, whether they originate from strains characterized by high or low frequencies of spontaneous mammary tumors;

(e) tumor-free lactating females exhibit the normally low levels of plasma gp 52 despite the fact that their milk contains an average of 20,000 ng/ml of this protein; and (f) the circulatory clearance time of gp 52 in tumorous animals is sufficiently rapid (a half-life of 4–6 hr.) to suggest a requirement for continued replenishment to maintain the high levels observed.

The MMTV model provides the basis for establishing the feasibility of utilizing a viral protein "marker" in plasma for monitoring the presence and status of human breast cancer. The use of a viral protein marker would be distinguishable from assays, such as disclosed in U.S. Pat. No. 3,999,944, which rely on detecting antigen induced leukocyte adherence inhibition caused by tumor specific cell mediated immunity.

DESCRIPTION OF THE INVENTION

The present invention relates to a method for detecting the presence and status of cancer in humans by assaying for certain tumor specific viral related proteins in plasma samples and novel reagents useful therein. Such method is thus useful in diagnosis as in initial screening programs for early detection of the disease, in therapy as in evaluating the status of the disease after surgical, radiation and/or chemotherapeutic treatment and in prognosis such as in detecting the possibility of recurrence or metastases.

Viral related proteins which can be employed as markers for the detection of cancer, particularly breast cancer, include viral enzymes such as RNA-dependent DNA polymerase (reverse transcriptase) or alternatively a tumor associated protein which is of viral origin.

A first aspect of the present invention therefore is directed to the detection of human breast cancer by utilizing RNA-dependent DNA polymerase as the plasma marker.

It has been previously known in the art that human breast tumor particles possess many of the features characteristic of RNA tumor viruses. In addition to the expected size (600S) and density (1.16 g/ml), these features include possession of an outer membrane and an inner one surrounding a "core" containing a DNA polymerase and a large molecular weight (70S) RNA possessing detectable homology to the RNA's of the mouse mammary tumor virus (MMTV) and of the Mason-Pfizer Monkey Virus (MPMV).

The purification and characterization of the DNA polymerase from the human breast cancer particles has now been accomplished and forms a part of the present invention. Key properties of this enzyme are very similar to those of the reverse transcriptases found in MMTV and MPMV. Thus, like these viral enzymes, the purified human breast cancer DNA polymerase exhibits the following three features that together distinguish the known viral reverse transcriptases from normal cellular DNA polymerases: (a) a strong preference for oligo(dT):poly(rA) over oligo(dT):poly(dA) as a template for the synthesis of poly(dT); (b) the acceptance of the highly specific oligo(dG):poly(rCm) as a template for the formation of poly(dG); (c) the ability to use a viral RNA (AMV) as a template to fashion a faithful DNA compelmentary copy. The resemblance of the human enzyme to the reverse transcriptases of MMTV and MPMV extends further in its possessing a molecular weight of 70,000 daltons and in its preference for $Mg^{++}$ over $Mn^{++}$. To date, an enzyme with these properties has not been detected in normal breast tissues or in benign tumors of the breast.

Isolation of human breast cancer DNA polymerase was accomplished by homogenizing breast cancer tissue and layering over discontinuous sucrose gradients. The density region at 1.16–1.19 g/cc was pooled, diluted, and centrifuged. Suspension of the pellets were fractionated by polyacrylamide agarose gel filtration. Fractions found active by DNA polymerase assay were pooled and chromatographed over a phosphocellulose column. Elution with a linear gradient of a 0.1 M to 0.5 M phosphate buffer pH 7.2. The main peak of polymerase activity was pooled and the enzyme concentrated by dialysis.

The purified human breast cancer DNA-polymerase can be utilized to develop a diagnostic assay for human breast cancer in a number of ways. It can be used to elicit human breast cancer DNA-polymerase specific antibodies by injecting the purified enzyme preferably in an emulsion of complete Freund's adjuvant into a suitable host animal such as a rabbit, guinea pig, goat, horse, etc. over a period of time and then bleeding the host (usually after booster injections have been given) to yield the desired antisera.

Additionally, the purified enzyme can be employed as a substrate for radioiodination to yield the [$^{125}$I] enzyme. A suitable procedure for radioiodination involves treating the enzyme with [$^{125}$I-]-3-(4-hydroxyphenyl)- propionic acid N-hydroxysuccinimide ester (Bolton-Hunter reagent) followed by purification over a G-100 column.

The aforesaid antibody and labelled enzyme can be utilized in a radioimmunoassay for human breast cancer DNA-polymerase in human plasma samples. Suitable radioimmunoassay procedures are known in the art. Thus, for example, an analogous procedure which can be employed is described by Ritzi et al., Virology 75, 188 (1976). In such procedure a buffered sample was treated with the antisera, i.e., rabbit anti-DNA polymerase and then after incubation for about 45 minutes at 37° C. the [$^{125}$I]-labelled enzyme was added. The sample was incubated for a further two hours at 37° C. and the bound radioactivity was separated from the free by the addition of normal IgG (rabbit) and a sufficient amount of second antibody (goat anti-rabbit IgG) to yield optimal precipitation of the IgG (rabbit).

The concentration of DNA-polymerase in the sample can be determined by comparing the counts of radioactivity observed in the bound and/or free fractions to a standard curve obtained by utilizing different known amounts of DNA-polymerase in the same assay procedure.

In an alternate procedure, the enzyme concentration in plasma samples can be determined by isolating the enzyme and measuring for enzymatic activity. Isolation can be readily accomplished by ammonium sulphate treatment of the plasma sample to precipitate the enzyme followed by affinity chromatography of the reconstituted precipitate through a column of sepharose bead to which a synthetic template for the enzyme had been covalently bonded. Suitable templates for this purpose include polyriboadenylate (poly(rA) or poly (2'-O-methylcytidylate) (poly(rCm). Elution of the enzyme from the column is accomplished using a gradient of 0.01 M KCl to 1.0 M KCl in 0.01 M phosphate buffered at pH 7.2. The DNA-polymerase activity of the isolated enzyme can be assayed using the same assay procedures employed in following the purification of the enzyme from breast cancer tissue discussed previously.

A further embodiment of the method of the present invention relates to the discovery of a human tumor associated protein which is of viral origin. One such protein can be demonstrated in substantial concentration in the intercellular spaces of human breast cancer tissue specimens and also circulating in the plasma of breast cancer patients. Tumor associated protein appears to be excess protein produced either by the virus after it has infected the breast cell or by the cell itself under viral control. It is therefor a further aspect of this invention to assay for the presence of this tumor associated protein in plasma samples as a diagnostic and prognostic test for cancer, such as, breast cancer.

The isolation of tumor associated protein from homogenized cancer tissue can be carried out by a combination of affinity chromatography and column chromatography. The affinity column comprises Concavalin A coupled to Sepharose 4B and is an article of commerce (Con A Sepharose). Elution of the protein from the affinity column is accomplished using buffered α-methyl-D-mannoside solution. Additional purification of the protein is accomplished by DEAE cellulose chromatography. The aforesaid procedures are directly analogous to the procedures employed by Ritzi et al., Virology 75, 188 (1976) for purification of gp 52 from MMTV and are described in greater detail therein.

The purified tumor associated protein of viral origin can be utilized in the same manner as described previously for DNA-polymerase for the development of a radioimmunoassay useful in the detection of breast cancer. Thus, the protein can be injected into host animals in a known manner to elicit antibodies specific to the tumor associated protein of viral origin. Moreover, the purified tumor associated protein can be radiolabelled, preferably radioiodinated with [$^{125}$I] Bolton-Hunter reagent to yield the labelled protein, i.e., $^{125}$I-tumor associated protein used as the marker in such radioimmunoassay. The radioimmunoassay procedure used in this aspect of the invention is not narrowly critical and any conventional technique can be employed. Preferably, the assay procedure employed will be the blocking double antibody procedure used for the radioimmunoassay of DNA-polymerase, described previously above.

In a further aspect of the present invention, it has now been discovered that Mason-Pfizer Monkey Virus (MPMV) or murine mammary tumor virus (MMTV) specific antibodies cross-react at reasonably high levels with both human breast cancer DNA-polymerase and human breast cancer viral origin tumor associated protein. It is thus possible to utilize such antibodies and radiolabelled antigen, preferably $^{125}$I-MPMV or $^{125}$I-MMTV, in the human breast cancer radioimmunoassays of this invention. Since MPMV and MMTV can be grown in tissue culture and thus are readily available in substantial amounts, this provides an especially convenient source of reagents for the wide-scale application of this invention.

In yet another aspect of the invention a suitable enzyme is covalently bound to a desired first or second antibody. The antibody-enzyme complex is still enzymatically active and when placed in contact with tissue specimens that contain the proper antigen the antibody-enzyme complex combines with it or the antigen-first antibody reaction product. A substrate of the enzyme is then added which results in the release of a colored precipitate at the site of activity. As used herein, the term "second antibody" is meant to include IgG derived from a mammalian host of a different species than the host used to elicit the first antibody, innoculated with the first antibody, which IgG will thus contain sites which will specifically bind to said first antibody, i.e., either MPMV or MMTV. In specific embodiments horseradish peroxidase was coupled to antibodies against Mason-Pfizer viral proteins and to goat anti-rabbit IgG. The appearance and distribution of the colored product enable not only the identification of the presence of the antigens, but to actually localize it in the malignant cells in the tissue specimens.

Another method employing this principle involves the quantitative estimate of the same antigens in the body fluids (e.g., plasma). The procedure is as follows: (1) coat the antibody on a solid surface (e.g., polystyrene); (2) add a known volume of plasma from a patient to the tube and allow the antibody coated on the surface to pick up any of the relevant antigens present in the sample; (3) the sample is then removed and the tube washed; (4) add the antibody-enzyme complex and incubated for attachment; any unabsorbed enzyme-linked antibody is then washed out; and (5) add the chromogenic substrate which gives either the color or the fluorescence which can be measured to estimate the amount of tumor antigen present. Preferred enzymes which can be employed include alkaline-phosphatase and β-galactosidase, both of which have excellent chromogenic substrates.

Further details relating to procedures useful in the practice of this aspect of the invention are available in the prior art. See, for example, U.S. Pat. Nos. 4,002,532 and 4,016,043.

The several assays which form the method aspects of this invention may be utilized to detect the presence of breast cancer in humans. To effectuate such use a statistically significant number of blood plasma samples from clinically established breast cancer patients, from normal patients, and from patients with benign or non-breast cancer tumors are assayed by either the direct DNA-polymerase activity method, the DNA-polymerase immunoassay, or the tumor associated protein immunoassay. The concentration of marker protein found in these assays is markedly elevated in the case of the breast cancer plasma samples when compared to the levels found for the normal and non-breast cancer tumor samples. It is thus possible to draw an arbitrary control level line between concentration levels of marker protein in each assay method which corresponds to the presence of breast cancer and levels which correspond to normal or non-breast cancer states. An unknown plasma sample can then be evaluated for the possibility of breast cancer in the subject by assaying the sample in accordance with one of the methods of the present invention and determining whether the marker protein is present in a concentration in excess of the control level.

Alternatively, a patient's own levels of marker protein can serve as an internal control. Thus, a patient with a confirmed breast cancer can be assayed before and after the initiation of therapy. A marked drop in the level of the marker protein would be indicative of a favorable prognosis of the treatment. A subsequent substantial increase in the marker protein concentration levels would be indicative of a possible recurrence or metastases of the disease and would allow the attending physician to initiate therapy at an early time. Moreover, the effectiveness of such therapy could be monitored by the instant method.

Furthermore, the marker protein can be detected immuno-histologically using the direct or indirect immunoperoxidase procedure, thus assisting in cancer diagnosis by this technique.

The present invention is further illustrated by reference to the examples which follow.

EXAMPLE 1

Subcellular Fractionation of Breast Tumor Tissue

Depending of the amounts of material available, between 9 and 30 g of tumor were thawed, minced, suspended in four volumes of cold 5% sucrose (w/v)-TNE (0.01 M Tris-HCl, pH 8.0, 0.15 M NaCl, 3 mM EDTA) and blended in a Silverson homogenizer. The homogenate was centrifuged at $4000 \times g$ and then $10,000 \times g$ to remove nuclei and mitochondria, respectively. Trypsin was added to the post-mitochondrial supernatant to a final concentration of 0.5 mg/ml. After incubation at 20° for 10 min, proteolytic activity was inhibited by the addition of two polypeptides, lima bean trypsin inhibitor (one-fold excess) and Trasylol (100 KIU/ml). The sample was layered over discontinuous sucrose gradients composed of 6 ml of 50% sucrose-TNE and 8 ml of 25% sucrose-TNE. Following centrifugation at 25,000 rpm for 90 min at 4° in a Spinco SW-27 rotor, material at the 25/50% interface was collected, diluted with TNE, and layered over linear 20–50% sucrose-TNE gradients. The samples were centrifuged as above for 16 hr and the different density regions collected. The density region (1.16–1.19 g/cc) in which RNA tumor viruses localize was pooled, diluted, and centrifuged as above for 90 min. The resulting pellets were resuspended in approximately 0.6 ml of 0.1 M Tris-HCl, pH 8.0.

Six lots of tumors were processed for enzyme in the manner described. Four of these (A, B, C, and D) yielded enough enzyme to characterize. One preparation (A), a metastatic liver tumor, came from a single patient, all the others being pooled material from a number of different individuals.

Polyacrylamide Agarose Gel Filtration

The resuspended pellet was solubilized and disrupted at 0° for 15 min by the addition of KCl (to 0.4 M), DTT (dithiothreitol, to 0.01 M), and a non-ionic detergent such as Triton X-100 (to 0.6%). The sample, approximately 0.9 ml, was applied to a $0.9 \times 50$ cm column of polyacrylamide agarose gel (Ultrogel AcA44) equilibrated with 0.3 M potassium phosphate, pH 8.0, in buffer A (2 mM DTT, 1 mM EDTA, 0.02% Triton X-100, and 10% glycerol). Elution was with 0.3 M phosphate-buffer A at a flow rate of about 2 ml/hr. Fractions (0.5 ml) were assayed for DNA polymerase and terminal transferase activity as described below.

Phosphocellulose Chromatography

The peak fractions from the Ultrogel column were pooled (3 ml) and Trasylol was added to a concentration of 100 KIU/ml. The sample was dialyzed against 0.01 M potassium phosphate, pH 7.2, in buffer A until the phosphate concentration was less than 0.02 M and then was loaded onto a $0.9 \times 10$ cm phosphocellulose column (Whatman P-11) equilibrated with the same buffer. The column was washed with 30 ml of the 0.01 M phosphate buffer and the enzyme activity was eluted with a 120 ml linear gradient of 0.01 M to 0.5 M potassium phosphate buffer A, pH 7.2, at a flow rate of 14 ml/hr. Fractions (1.2 ml) were assayed for both DNA polymerase and terminal transferase activities. The main peak of polymerase activity was pooled and Trasylol was added to 100 KIU/ml. This enzyme fraction (called PC enzyme) was concentrated by dialysis at 0° against an osmotically active, high molecular weight synthetic polymer such as Aquacide 11-A.

Glycerol Gradient Centrifugation

For estimation of molecular weight, the concentrated PC enzyme was diluted three-fold with 0.1 M potassium phosphate, pH 8.0, and layered on a linear 10–30% glycerol gradient containing 0.1 M potassium phosphate, pH 8.0, 2 mM DTT, and 0.02% Triton X-100. Centrifugation was at 48,000 rpm for 12 hr at 1° in a Spinco SW-50.1 rotor. Fractions were collected from the bottom and assayed for reverse transcriptase activity with oligo(dG):poly(rC) as template. Bovine serum albumin served as a sedimentation marker in a parallel gradient.

DNA Polymerase Assays

Assay mixtures for polymerase activity with synthetic polymer templates contained (in 100 $\mu$l): 5 $\mu$mol Tris-HCl, pH 8.0, 0.5 $\mu$mol MgCl$_2$, 0.1 $\mu$mol DTT, and the following combinations of polymer and dNTPs-0.4

μg oligo(dG):poly(rC) or oligo(dG):poly(rCm), 0.02 μmol dCTP and 1.0 nmol [$^3$H] dGTP (4000 cpm/pmol); 0.4 μg oligo(dT):poly(rA) or oligo(dT):poly(dA), 0.02 μmol dATP and 1.0 mmol [$^3$H] dTTP (4000 cpm/pmol). In reactions with oligo(dG):poly(rCm), MnCl$_2$ (0.02 μmol) replaced MgCl$_2$.

Assays employing AMV RNA contained (in 100 μl): 5 μmol Tris-HCl, pH 8.0, 0.8 μmol MgCl$_2$, 0.1 μmol DTT, 10 μg actinomycin D (Sigma Corp.), 5 μg distamycin A (Calbiochem), 2 μg AMV 70S' RNA, 0.1 μg oligo(dT)$_{12-18}$, 0.1 μmol each of dATP, dGTP, and dTTP, and 5 nmol [$^3$H] dCTP (1.5×10$^4$ cpm/pmol).

All reactions were incubated at 36° for 15–30 min and were terminated by the addition of 0.5 ml cold 0.067 M sodium pyrophosphate-1 M sodium phosphate, pH 7.2, followed by 0.5 ml cold 80% TCA. Acid-insoluble radioactivity was collected on membrane filters and measured in a scintillation counter.

Terminal deoxynucleotidyl transferase activity was measured by the polymerization of [$^3$H] dGTP in the absence of a complementary polymer template. Reactions were carried out as described above except that polymer dNTP combination was replaced with 0.4 μg oligo(dG)$_{10-18}$ plus 0.02 μmol dCTP and 1.0 nmol [$^3$H] dGTP.

All synthetic oligo- and polynucleotides tritiated dGTP, dTTP, and dCTP were articles of commerce. AMV 70S RNA was isolated from the purified virus as described in Marcus et al., Virology 71, 242 (1976).

Hybridization Reactions

Procedures for the hybridization reactions and their analysis with S$_1$ nuclease have been reported by Weiss et al. supra. Conditions for Cs$_2$SO$_4$ equilibrium density centrifugation as disclosed by Axel et al., Nature 235, 32 (1972) were modified by the addition of 0.02% sodium N-lauroyl sarcosinate and 20 μg each of *E. coli* DNA and RNA to the gradients.

Results

The data described below are based on independent enzyme isolations from four different tumor collections (labeled A through D). The behavior during fractionation and the properties of the breast tumor polymerase did not vary significantly from one preparation to another.

Polymerase preparation A was isolated from a metastatic lesion in the liver of a patient with breast cancer. Nine grams of tumor were homogenized and the particulate material, banding at a density of 1.16–1.19 g/ml, was collected as described above. The recovered pellet was solubilized by the addition of Triton X-100 and then fractionated through a polyacrylamide-agarose gel (Ultrogen ACA-44) column. Each column fraction was assayed for (1) DNA polymerase with oligo(dG)$_{12-18}$:poly(rC) as a template and (2) for terminal transferase, using oligo(dG)$_{12-18}$ as a primer. Three peaks (two major and one minor) of DNA polymerase activity were observed and it was evident that the first major peak also contained terminal transferase. The two major peaks were found (Table 1) to contain 90% of the applied polymerase activity and 3% of the protein as measured by the fluorescamine procedure of Udenfriend et al., Science 178, 871 (1972).

TABLE 1.

Purification of DNA polymerase from a human breast tumor (Sample A)

| | Total Protein (mg) | Total Activity (pmol) | Specific Activity (pmol/mg) |
|---|---|---|---|
| 1. Viral density region | 8.3 | 168 | 20 |
| 2. Polyacrylamide agarose | 0.25 | 148 | 5.6 × 10$^2$ |
| 3. Phosphocellulose | 0.02 | 96 | 4.8 × 10$^3$ |

All reactions contained oligo(dG):poly(rC) as template and were incubated for 30 min at 36°. Total activity was calculated as pmol [$^3$H]dCMP polymerized.

To examine the reality of the separation of the polymerase activities observed above, the two major peaks were pooled, dialyzed to reduce the phosphate buffer concentration, and then chromatographed through a phosphocellulose column (PC) with a linear (0.01 M to 0.5 M) phosphate gradient. The polymerase activities were seen to again resolve into two major peaks, one eluting at 0.08 M phosphate and the other at 0.18 M. It will be noted that again the second major polymerase peak is devoid of terminal transferase activity. The latter splits into two peaks, one associated with the first DNA polymerase activity at 0.08 M phosphate, and another eluting by itself at 0.23 M phosphate.

The second (0.18 M phosphate) peak of polymerase activity observed on the PC column is not found in normal tissues (3 samples of breast tissue and 3 samples from spleens) or in benign fibroadenomas of the breast (3 pools of 3–4 fibroadenomas each) and is thus the DNA polymerase unique to breast cancer tissue. The fractions composing peak 2 of the PC column are found to contain 65% of the applied DNA polymerase activity and 8% of the protein. These fractions are pooled and concentrated as described above to yield the breast tumor polymerase. Table 1 summarizes the yields of activity and protein at each of the three steps in a typical purification.

EXAMPLE 2

Evidence that the Breast Cancer Polymerase is a Reverse Transcriptase

There are several useful criteria which distinguish the reverse transcriptases of the RNA tumor viruses fom normal mammalian DNA polymerases. The viral reverse transcriptases show a preference for oligo(dT) poly(rA) over oligo(dT):poly(dA) and they also accept oligo(dG):poly(rC) and oligo(dG)poly(rCm) as excellent templates for the synthesis of poly(dG). Another, and more diagnostic characteristic, is the ability of a reverse transcriptase to use a heteropolymeric RNA to direct the synthesis of a faithful complementary DNA as demonstrated by proper back-hybridization of the cDNA product to the template used in the synthesis.

The responses of four of the breast cancer polymerases to the synthetic polyribonucleotides are summarized in Table 2. The results show a pattern of activities completely consistent with that obtained with reverse transcriptases isolated from authentic animal RNA tumor viruses. Thus, in all cases, oligo(dT):poly(rA) is superior to oligo(dT):poly(dA) for the synthesis of poly(dT). Further, both oligo(dG):poly(rC) and oligo(dG):poly(rC$_n$) were excellent templates for the formation of poly(dG). It should be noted that in addition to the four breast tumor enzyme preparations described here, many others (more than 50) obtained from additional patients in an ongoing effort have been examined in the same way at different stages of purity using various methods of fractionation and they all exhibited the response pattern described in Table 2.

TABLE 2.

Synthetic polynucleotides as templates for the breast tumor polymerase

| Template | [$^3$H]dNTF | pmol [$^3$H]dNMP polymerized | | | |
|---|---|---|---|---|---|
| | | Prep. A | Prep. B | Prep. C | Prep. D |
| oligo(dT): poly(rA) | T | 0.472 | 0.445 | 0.221 | 0.495 |
| oligo(dT): poly(dA) | T | 0.044 | 0.021 | 0.062 | 0.071 |
| oligo(dG): poly(rC) | G | 0.534 | 0.444 | 0.180 | 0.532 |
| oligo(dG): poly(rCm) | G | 0.502 | 0.410 | N.T. | N.T. |
| oligo(dG) | G | 0.010 | 0.008 | N.T. | N.T. |

Polymerase reactions were performed with the indicated template as described above.

Incubation was at 36° for 15 min (Prep. C) or 30 min (Preps. A, B and D). Polymerase Prep A was isolated from a single tumor (9 g), B from a pool of 3 tumors (14 g), C from a pool of 4 tumors (32 g) and D from a pool of 5 tumors (61 g).

The operational definition of a reverse transcriptase requires the demonstration that it can use a heteropolymeric RNA to make a DNA transcript. The response (Table 3) of the breast cancer polymerase to the RNA of the avian myeloblastosis virus (AMV) is that expected from the synthesis of a heteropolymeric DNA. Leaving out any one, or all, of the required three unlabeled deoxyribosidetrisphosphates leads to the same virtual disappearance of synthetic activity as occurs on omission of the RNA template.

TABLE 3.

Deoxynucleoside triphosphate and RNA requirements of the breast tumor DNA polymerase

| Reaction | pmol [$^3$H]dCMP polymerized | |
|---|---|---|
| | A | B |
| 1. Complete | 0.200 | 0.170 |
| 2. -dATP | 0.013 | 0.011 |
| 3. -dGTP | 0.025 | 0.022 |
| 4. -dTTP | 0.012 | 0.005 |
| 5. -dATP, dGTP, dTTP | 0.008 | 0.011 |
| 6. -RNA | 0.026 | 0.016 |

Polymerase preparations A and B were assayed for RNA-dependent DNA synthesis with AMV RNA as the template. The reactions, were incubated at 36° for 30 min under the conditions given in Example 1.

The most telling test of a putative reverse transcriptase reaction comes from an examination of the fidelity of the DNA transcript. This requires isolation of the [$^3$H] DNA product and challenging it in annealing reaction with the RNA template used in the synthesis. To this end, a 2-ml reaction was run for 15 min with the DNA polymerase preparation A and AMV-RNA as the template, leading to the synthesis of approximately 3 ng [$^3$H] DNA at $2 \times 10^7$ cpm/ug. The [$^3$H] DNA product was purified and recovered by the usual procedures and then annealed with AMV and RLV 70S PNAs. The outcome was examined by separation in $Cs_2SO_4$ gradients and by resistance to $S_1$ nuclease. Both methods yielded less than 5% annealing to the unrelated RLV-RNA and between 80 and 85% hydribidzation to AMV-RNA, the template used to direct the synthesis. These results suggest therefore that the [$^3$H] DNA is a single-stranded complement of the AMV-RNA. A more informative examination of the [$^3$H] DNA product is provided by a kinetic examination of the annealing reaction. A comparison was made of the annealing kinetics to AMV-RNA of two [$^3$H] DNA products, one synthesized under the direction of AMV-RNA by AMV reverse transcriptase and the other synthesized by the human breast cancer polymerase instructed by the same template. It was found that the kinetics of annealing to AMV-RNA of the two DNA products are indistinguishable. Thus, the human enzyme is every bit as efficient in reverse transcribing AMV-RNA as is the homologous reverse transcriptase purified from the avian virus.

EXAMPLE 3

Other Properties of the Breast Cancer Polymerase

Variations in temperature and pH were examined for their effects on the activities of several preparations of the breast cancer polymerase using oligo(dG):poly(rC) and oligo(dT):poly(rA) as templates. The maximal rate of polymerization occurred at 37° in 5 mM $MgCl_2$ over a pH range of 7.0 to 8.5.

The divalent ion requirements of reverse transcriptases are of some interest since they serve to divide the viruses of origin into different groups. Thus, all six strains of MMTV from a variety of sources contain a reverse transcriptase showing a strong preference for $Mg^{++}$ as compared with $Mn^{++}$. The same holds true for the Mason-Pfizer monkey virus, the bromodeoxyuridine-induced guinea pig virus and the bovine leukemia virus. In contrast, the reverse transcriptases of the murine leukemia and sarcoma viruses function much more effectively in the presence of $Mn^{++}$. For the human breast cancer enzyme, $Mn^{++}$ at its optimum yields only about one seventh of the activity attainable with $Mg^{++}$. It is clear that as between the murine mammary tumor and leukemia viruses, the human breast cancer enzyme shows a divalent ion requirement most closely resembling the mammary tumor virus reverse transcriptases.

The molecular size of the breast cancer enzyme was estimated by sedimentation through a linear (10–30%) glycerol gradient. The enzyme was located by assaying fractions with AMV-RNA as template. The enzyme activity sediments between 5S and 6S, slightly faster than the bovine serum albumin marker, placing the molecular weight at around 70,000 daltons. This result is also consistent with the relative elution positions of these same proteins on ultrogel. A number of enzyme preparations from different breast tumor sources yielded identical sedimentation values.

EXAMPLE 4

Materials and Methods

Viruses

Mason-Pfizer monkey virus was propagated in a suspension culture of the normal human lymphocytic cell line NC-37 and concentrated as previously described by Schlom and Spiegelman. Proc. Nat. Acad. Sci. U.S.A. 68, 1613 (1971). The virus was further purified by centrifugation through an 8-ml column of 20% glyercol in TNE buffer (0.01 M Tris-HCl, pH 8.3, 0.15 M NaCl, 0.002 EDTA) onto a pad of 100% glycerol at 98,000×g for 60 min at 4°. The viral pellet was taken up in TNE buffer and spun to equilibrium in a continuous 20–50% sucrose gradient in TNE at 98,000×g for 16 hr. The particles banding between densities of 1.14–1.19 g/ml were collected, diluted, and centrifuged at 98,000×g for 45 min at 4°. The pellet was used immediately for DNA polymerase purification.

Avian myeloblastosis virus (AMV, BAI strain-A), simian sarcoma virus strain-1 (SSV-1), Friend leukemia virus (FLV), feline leukemia virus (FeLV), and Rauscher leukemia virus (RLV) were also used in this Example. All viral concentrates were purified as described above.

Preparation of RNA-instructed DNA Polymerase from Human Malignant Breast Tumor Reverse transcriptase from human malignant breast tumor was prepared as previously described by Ohno et al., Proc. Natl. Acad. Sci. U.S.A. 74, 764 (1977) from particles purified by isopycinc separation. After disruption by incubation in 0.2% Triton X-100 for 15 min at 0°, some of the samples were analyzed for endogenous polymerase activity as well as oligo(dG):poly(rC) and oligo(dT):poly(rA) directed synthesis of poly(dG) and poly(rA), respectively. The disrupted virus density regions chromatographed on a polyacrylamide agarose column (Ultrogel AcA44, LKB,Co.) and the eluted enzyme peak loaded on a phosphocellulose (Whatman p11) column. The enzyme was eluted with 0.01 to 0.5 M potassium phosphate gradient and concentrated as described by Ohno et al. supra.

Preparation of Viral Regions from Human Leukemia and Hodgkin's Spleen

Spleens from patients with human chronic lymphocytic leukemia (CLL), chronic myelogenous leukemia (CML), and Hodgkin's lymphoma were used as the sources of viral density region preparations, and the polymerase activities were analyzed by endogenous kinetics as described by Witkin et al., Proc. Natl. Acad. Sci. U.S.A. 72, 4133 (1975).

Preparation of MPMV Polymerase

The MPMV pellet prepared as described above (viruses) was resuspended onto 0.05 M Tris-HCl, pH 9.2, 0.001 M EDTA and 2 M KCl, sonicated, and then centrifuged at 98,000×g for 120 min. The pellet was used to prepare purified DNA polymerase by column chromatography as described previously by Witkins et al., supra.

Preparation of Antiserum

Antiserum against MPMV-DNA was induced in New Zealand white rabbits. Three cycles of immunization were required to achieve the desired titer of anti-polymerase IgG. In each cycle the enzyme ($1 \times 10^3$ pmoles of TMP incorporated per min) was emulsified with an equal vol of Freund's adjuvant and injected into the two hind footpads. This was followed by two additional similar inoculations given at two-week intervals in the same sites.

Sera were fractionated by chromatography on a Sephadex G-200, 0.1 M Tris-HCl, pH 8.0. Rabbit gamma globulins were identified serologically by immuno-diffusion with goat anti-rabbit IgG antiserum. The relevant fractions were concentrated by ammonium sulfate precipitation (50% saturation) and dialyzed against 0.1 M Tris-HCl, pH 8.0. The protein concentration of the IgG fraction was measured by the Lowry procedure.

DNA Polymerase Assays

Assay mixtures for polymerase activity with synthetic polymer templates contained (in 100 ul): 5 umol Tris-HCl, pH 8.0, 0.5 umol MgCl$_2$, 0.1 umol DTT, and the following combinations of polymer and dNTPs: 0.4 ug oligo(dG):poly(rC) or oligo(dG):poly(rCm), 0.02 umol dCTP and 1.0 nmol [$^3$H] dGTP (4000 cpm/pmol), 0.4 ug oligo(dT):poly(rA) or oligo(dT):poly(dA), 0.02 umol dATP and 1.0 nmol [$^3$H] dTTP (4000 cpm/pmol). In reactions with oligo(dG):poly(rCm), MnCl$_2$ (0.02 umol) replaced MgCl$_2$.

Assays using endogenous RNA contained (in 100 ul): 5 umol Tris-HCl, pH 8.0, 0.8 umol MgCl$_2$, 0.1 umol DTT, 10 ug actinomycin D, 5 ug distamycin A, 0.1 ug oligo(dT)$_{12-18}$, 0.1 umol each of dATP, dGTP, and dTTP, and 5 nmol [$^3$H] dCTP ($1.5 \times 10^4$ cpm/pmol).

All reactions were incubated at 36° for 15–30 min as indicated, and were terminated by the addition of 0.5 ml cold 0.067 M sodium pyrophosphate, 1 M sodium phosphate, pH 7.2, followed by 0.5 m. cold 80% TCA. Acid-insoluble radioactivity was collected on membrane filters and measured in a scintillation counter.

Terminal deoxynucleotide transferase activity was measured by the polymerization of [$^3$H] dGTP in the absence of a complementary polymer template, the latter being replaced by 0.4 ug oligo(dG)$_{10-18}$.

The Effect of Antibody on DNA Polymerase Activities

Reaction mixtures for the neutralization of DNA polymerase activity (total vol 55 ul) contained in addition to 25 ug of bovine serum albumin (BSA) and DNA polymerase, the indicated amount (25–150 ug) of purified IgG fraction. The buffer used was 0.01 M Tris-HCl, pH 8.0, 0.15 M of potassium chloride. After 15 min incubation at 4°, a polymerase assay was carried out using oligo(dG):poly(rC) as described above. In certain instances, the effect of antibody on the activity by the endogenous RNA was examined.

Detection of Antibody-enzyme Complexes in Glycerol Gradients

The concentrated enzyme (reverse transcriptase from MPMV or from human malignant breast tumors) fractions were diluted three-flow with 0.1 M potassium phosphate, pH 8.0, containing 0.5 mg/ml of bovine serum albumin, and the indicated amounts of purified IgG fractions were added. After incubation for 15 min at 4°, the samples were layered over a 10–30% glyercol gradient adjusted to 0.1 M potassium phosphate, pH 8.0, 0.002 M dithiothreitol and 0.02% Triton X-100. The samples were sedimented at 48,000 rpm for 12 hr in a Spinco SW50-1 rotor at 1°. Fractions were collected dropwise from the bottom of the tubes and the enzyme activity assayed as described above.

Results

A Comparison of the Effects of Anti-MPMV DNA Polymerase IgG on a Variety of Polymerases The effects of the anti-MPMV DNA polymerase on a number of viral DNA polymerases and on the corresponding enzyme of the human breast cancer particles were compared. In these experiments, isopycnically banded particles, purified as described in Materials and Methods, were employed as a source of the DNA polymerase and oligo(dG):poly(rC) was used as the template. The antibody inhibits the MPMV-DNA polymerase more than 80% and achieves a 26% inhibition of the DNA polymerase associated with the human breast cancer particles. In contrast, no detectable effect is observed on the DNA polymerases of any of the other animal oncornaviruses, including avian myeloblastosis virus (AMV), Rauscher and Friend murine leukemia viruses (RLV and FLV), feline leukemia virus (FeLV), a simian sarcoma virus (SSV-1), or murine mammary tumor virus (MMTV).

Specificity of the Inhibition by the Anti-MPMV Polymerase IgG

The next issue examined centered on whether the inhibition observed with the breast cancer particle enzyme was confined to this malignancy. As already known in the art; spleens from patients with mesenchyma cancers contitute a convenient source of particle enzyme, and these were chosen for mmunologic comparison. The particle fractions were prepared and the endogenous polymerase activities were assayed as previously described for human breast tumors and for spleens involved in mesenchymal neoplasias. At least five instances of each kind of neoplastic tissue were examined and typical results are shown in Table 1.

TABLE 1.

The effect of anti-MPMV polymerase IgG on endogenous reverse transcriptase activities of particles from human malignant tissues.

| Cells or Tissues | Normal IgG 100 μg/0.1 ml cpm | BSA 100 μg/0.1 ml cpm | % | Anti-MPMV IgG 100 μg/0.1 ml cpm | % | RNase 8 μg/0.1 ml cpm | % |
|---|---|---|---|---|---|---|---|
| Breast Cancer Ex. 1 | 1862 | 1748 | 93.8 | 765 | 41.1 | 331 | 17.7 |
| Breast Cancer Ex. 2 | 3682 | 3429 | 93.1 | 138 | 3.7 | 195 | 5.3 |
| Breast Cancer Ex. 3 | 2340 | 2118 | 90.5 | 283 | 12.1 | 321 | 13.7 |
| CHL-Spleen | 3086 | 3110 | 100.7 | 2806 | 90.9 | 168 | 5.4 |
| CLL-Spleen | 1540 | 1640 | 106.5 | 1621 | 105.2 | 126 | 8.2 |
| Hodgkin Spleen | 1261 | 1205 | 95.5 | 1018 | 80.7 | 186 | 14.8 |

Reaction mixtures (50 μλ) contained 50 μg of either anti-MPMV-polymerase IgG, or normal rabbit IgG, or bovine serum albumen (BSA) and detergent disrupted particles. Incubation to permit complex formation with antibody was carried out for 15 min at 0°. The endogenous enzyme activity was then measured at 37° for 15 min as described in Methods. The sensitivity to RNase (80 μg/ml) was also examined.

Significant inhibitions are not seen with the particle enzymes derived from the leukemic and the lymphoma spleens. However, the breast cancer particulate enzymes were inhibited from 59% to over 95%. Note that these endogenous reactions are more severely affected by the anti-MPMV polymerase IgG than the synthesis directed by synthetic templates. As expected, all the DNA polymerase activities described in Table 1 are sensitive to RNase and resistant to the presence of actinomycin D (100 ug/ml) and distamycin (50 ug/ml), features characteristic of RNA-directed DNA polymerase.

The data shown in Table 1 were obtained with the endogenous reactions of detergent-disrupted particles isolated from the indicated neoplastic tissues. For completeness a similar comparison was carried out using the corresponding purified enzymes directly by oligo(dG)-:poly(rC). Experiments using this approach provided the responses to anti-MPMV polymerase IgG of the reverse transcriptases purified from the particles prepared from breast cancers and from a chronic myelogenous leukemic spleen. Over the whole concentration range of IgG examined, the leukemic reverse transcriptase is not significantly affected. In contrast, the anti-MPMV polymerase IgG does suppress the activity of the breast cancer reverse transcriptase at all concentrations tested, achieving a 37% inhibition at 150 ug per reaction mixture.

Table 2 examines another aspect of the specificity of the interaction by testing the responses of normal cellular DNA polymerases to the anti-MPMV polymerase IgG.

TABLE 2.

Effect of anti-MPMW IgG on cellular and breast tumor particle polymerases.

| Source (Enzyme) | Normal IgG (75 μg/0.1 ml) cpm | Anti-MPMV polymerase IgG (75 μg/0.1 ml) cpm | % of Control |
|---|---|---|---|
| Breast tumor (Reverse transcriptase) | 1628 | 662 | 40.7 |
| Breast tumor (DNA polymerase γ) | 2166 | 2196 | 101.4 |
| Hela Cell (DNA polymerase γ) | 1865 | 2011 | 107.8 |
| Hela Cell (DNA polymerase β) | 1658 | 1819 | 109.7 |

The indicated DNA polymerases were assayed as described in Methods. The enzyme activity in the presence of normal rabbit IgG was taken as the control. Note that Table 1 compares normal IgG with BSA. Each 100 μl of assay mixture contained 0.4 μg of oligo(dT):poly(rA) and incubation was for 30 min at 37°.

Neither preparation of DNA polymerase γ, whether isolated from a breast tumor or from the HeLa cell strain, was detectably inhibited, and the same was true for DNA polymerase β. At the same level the anti-MPMV polymerase IgG suppressed the breast cancer reverse transcriptase by 40%. Similar experiments were carried out with the normal DNA polymerase α and again have found no evidence of inhibition by the anti-MPMV polymerase IgG.

The Demonstration by Sedimentation of Complexes between the Breast Cancer DNA Polymerase and the Anti-Polymerase IgG It was desirable to see whether further evidence could be provided for the existence of physical complexes between the breast cancer reverse transcriptase and the anti-MPMV polymerase IgG. First, such evidence would add direct support to the conclusions derived from simple suppression of enzyme activity. Second, experiments along these lines could identify the basis underlying the apparent inability of the anti-MPMV DNA polymerase IgG to achieve total neutralization of the breast cancer reverse transcriptase activity. Basically, two mechanisms can be offered to explain the incompleteness of the inhibition. One would suggest that the enzyme preparation is heterogeneous and that only a sub-population forms inactive complexes with the added IgG. The other would assume that the population of enzyme molecules is homogeneous in this respect and that all form complexes, which can, however, express a fraction of the original activity. These two possibilities are readily distinguishable by a sedimentation analysis of the enzyme activity before and after reaction with the relevant IgG.

To monitor the effectiveness of this approach, a positive control experiment was carried out with the homologous system consisting of MPMV-DNA polymerase and its antibody. A negative control was included using normal (pre-immunized) IgG from the same rabbit. A $250\mu\lambda$ reaction containing enzyme and 150 ug of the indicated IgG were incubated at 4° for 15 min as described in Materials and Methods. The mixture is then layered on a 10 to 30% gradient and centrifuged at 48,000 rpm for 12 hr. at 1°. Fractions are then collected from the bottom and assayed for reverse transcriptase and for the presence of IgG by immunodiffusion. Incubation with normal IgG was found not to change the position (tube 13) of the peak of MPMV reverse transcriptase activity with respect to the external marker bovine serum albumin (BSA). The enzyme still sediments at a velocity corresponding to a molecular weight of 70,000 daltons. In this same gradient, the IgG was located in tubes 10, 11, and 12. Incubation of the polymerase with 150 ug of anti-MPMV polymerase results in an 80% loss of enzyme activity and a markedly different sedimentation pattern of the residual activity. No enzyme is detectable at the original position close to BSA, all of it appearing as complexes sedimenting faster than free enzyme or IgG. The IgG is now detected by immunodiffusion in fractions 13, 14, and 15 as well as in fractions 6 through 10, which encompass the peak of polymerase activity.

A very similar situation is obtained in the experiments with the reverse transcriptase purified from human breast cancer particles. Incubation with normal IgG leaves the human enzyme in its usual position (tube 15) within one tube of the BSA marker, and the IgG is found by immunodiffusion in tubes 12 to 14. However, reaction with anti-MPMV polymerase IgG results in a 4596 loss of activity and shifts the residue down the tube as fast-moving complexes found in fractions 6 through 10, in which IgG can also be detected by immunodiffusion. IgG is also found in its original position (fractions 12 through 14).

It is evident from the results described above that neither the MPMV reverse transcriptase nor the one isolated from human breast cancer particles contains a significant proportion of molecules unable to complex with anti-MPMV polymerase IgG. The fact that the enzyme IgG complexes can express some activity is not a new phenonmenon. Indeed, in some reported instances, such complexes are fully active.

Discussion

The experiments described here show that anti-MPMV DNA IgG, when present in excess, can completely complex with and partially inhibit the reverse transcriptase isolated from human breast cancer particles. The specificity of the inhibition is supported by the inability of this same antibody to affect the activities of normal cellular DNA polymerases or of a variety of reverse transcriptases from animal oncornaviruses (e.g., AMV, RLV, FLV, FeLV, SSV-1, and MMTV). Further, normal IgG obtained from the same rabbit prior to immunization does not complex with, or inhibit, either the MPMV or the human breast cancer reverse transcriptase.

Aside from its etiologic interest, the immunologic cross-reactivity between the reverse transcriptases of MPMV and of the human breast cancer particles has an implication of more immediate import. It provides the basis for examining human breast cancer by procedures of clinical usefulness. MPMV can be produced in tissue culture in yields adequate for purification of its enzyme and other protein components. These can in turn be used to generate antisera for use as specific detecting reagents in immunofluorescent and immunoperoxidase staining of frozen sections as diagnostic aids for surgical pathologists. Of further interest is the use of such development in immunoassays for the systemic detection of immunologically related protein in the plasma and other body fluids of patients with cancers, other than breast cancer such as lung cancer, stomach, rectal and colon cancers, ovarian cancer, brain cancer, bone cancer, cancer of the lymph glands, skin cancer (squamous cell and basal cell carcinomas and melanoma) and the like. Each of these cancers has its own distinctive particle associated protein.

EXAMPLE 5

Materials and Methods

Tissues. Paraffin blocks of tissues used for diagnostic purposes were obtained from the files of the Divisions of Surgical, Gynecologic and Anatomic Pathology of the College of Physicians and Surgeons of Columbia University. Blocks of normal, benign and malignant breast tissues were selected from biopsies, resections, mastectomies and reduction mammoplastics. Four autopsy cases of disseminated carcinoma were also used. Cases of non-breast malignancies included biopsies and resection specimens. Whenever available, multiple blocks from each case were used. All of these were initially fixed in Bouin's fixative or, in the case of larger specimens, in 10% buffered formalin followed by Bouin's fixation.

In all cases $5\mu$ serial sections were cut for immunohistochemical staining, and at least one section from each block was stained with hematoxylin and eosin for routine histopathologic examination. Sections of mammary tumors from Paris RIII or $CD8F_1$ mice, processed as follows, were always included as positive controls.

Immediately after excision, each tumor sample was divided into two parts. One was snap frozen in dry ice and 5-methylbutane, and the other was cut into 2–4 mm sections which were fixed in Bouin's fixative for at least 24 hours after which they were routinely dehydrated and embedded in paraffin. Cryostat sections at $6\mu$ were cut from the frozen blocks, picked up on albumin-coated slides, and were fixed for at least 30 minutes in cold Bouin's prior to immunohistochemical staining.

Immunohistochemical Staining. The indirect immunoperoxidase method was used on the human material. A preliminary step was used involving an incubation with hyaluronidase (600 units/ml) at 37° for one hour. This enzymatic pretreatment was found to minimize nonspecific background staining of collagenous stroma. It did not interfere with the specific staining of the human or murine malignant cells, as determined by the use of parallel nontreated controls. The sections were deparaffinized and rehydrated in xylene and graded alcohols and the picric acid (from the Bouin fixative) was removed by lithium carbonate. After rinsing and thoroughly washing the sections in 0.1 M phosphate buffered saline (PBS), pH 7.6, for 10 minutes with stirring, the tissues were incubated with undiluted normal goat serum at 37° for 10 minutes. This preliminary incubation is an attempt to saturate Fc receptors and to block other nonspecific affinities in the tissue for the primary antibody. After a gentle rinse in PBS, the tissues were incubated with primary antibody (rabbit α-MMTV or rabbit β-gp52 at 50 μg/ml in PBS) for 20 minutes at 37°. After several rinses and a 10 minute wash in PBS, the secondary antibody (peroxidase-conjugated goat anti-rabbit IgG at 100 μg/ml in whole goat serum) was applied for 30 minutes at room temperature. After rinsing and washing as before, the tissues were submerged for 10 minutes at room temperature in a saturated solution of 3,3'-diaminobenzidine (50 mg. of free base in 100 ml. of PBS) to which had been added hydrogen peroxide (0.003%) just prior to use. The sections were then washed, lightly counterstained in dilute methylene blue, dehydrated in graded alcohols and xylene, and mounted with Permount.

IgG Preparations. The indirect immunoperoxidase technique requires the use of two antibodies. The primary one detects the antigen being sought and the second antibody, to which the peroxidase is conjugated, is directed against the first antibody. The primary IgG (α-MMTV) is derived from a rabbit immunized with MMTV isolated from the milk of Paris RIII mice. The second antibody is goat anti-rabbit IgG which is conjugated to peroxidase.

The two principal antisera used were raised in rabbits using whole MMTV isolated from the milk of Paris RIII strain and gp52 purified from the same virus as described by Ritzi et al., Virology, 75, 188 (1976). The IgG preparations from these are designated as α-gp52 (RIII) and α-MMTV (RIII). Other antisera used as checks included α-MMTV (C3H), a rabbit antiserum against MMTV derived from the C3H mouse strain and α-gp52 raised in goats.

The γ-globulin (IgG) fractions were purified from the above antisera by sodium sulfate fractionation followed by ion exchange chromatography on DEAE-cellulose. The IgG samples thus purified had an $A_{280}:A_{250}$ ratio of about 2.5 and were judged more than 95% pure by SDS-polyacrylamide gel electrophoresis.

Conjugation of IgG to Peroxidase. Horseradish peroxidase (HRPO), (Sigma Type VI, Rz, 3.27–3.47) was linked to purified goat anti-rabbit IgG by the procedure of Nakane and Kawaoi, J. Histochem. Cytochem. 22, 1084 (1974) with the following modifications: (1) it was found that the use of phenylisothiocyanate to block free amino groups enhances sensitivity and avoids the nonspecific staining often observed with 1-fluoro-2,4-dinitrobenzene blocking; (2) stabilization of the Schiff's base of the conjugate by reduction with borohydride needs to be carefully controlled to avoid formation of insoluble flocculant material. The minimum amount of borohydride needed was determined by titration to the point where the peroxidase-aldehyde IgG mixture developed a slight reddish tinge due to reduction of the heme group. Thus, in a conjugation involving 5 mg. peroxidase and 7.5 mg. IgG, about 0.3–0.5 mg. borohydride was needed to obtain optimal results; (3) after the borohydride reduction step, the conjugate was separated from any free enzyme by an ammonium sulfate precipitation at 0.5 saturation. Time-consuming purification procedures involving gel filtration or density gradient centrifugation did not seem to be necessary.

Immunoabsorbants and their Preparation. A rigorous test of the specificity of any staining reaction observed in the human tissues requires absorption with relevant viral antigens as well as with a variety of substances containing antigens that might be detected by the antibodies being used and which would be irrelevant to the presence or absence of viral-related proteins. The absorbants were used in either the insoluble or soluble state depending upon convenience and the amounts of material available. Insoluble absorbants were prepared by cross-linking the proteins with glutaraldehyde from the following: (a) pooled normal human plasma; (b) fetal calf serum; (c) pooled normal human breast tissue extracts; (d) normal human milk; and (e) humun lung collagen. In addition, sheep red blood cells and pooled human lymphocytes were treated with glutaraldehyde. Insoluble absorbants were used at a concentration of 30 mg. of lyophilized powder per ml. containing 1 mg. of the IgG.

Viruses used as absorbants included: (a) MMTV (RIII) from the milk of Paris RIII mice; (b) MMTV ($C_3H$) grown in feline kideny cells (CrFeK); (c) MMTV ($C_3H$) grown in $C_3H$ mouse cells (MM5T); (d) Rauscher leukemia virus (RLV) grown in the JLSV9 cell line; (e) Rauscher leukemia virus (RLV) purified from the plasma of Balb/C mice; (f) Mason-Pfizer monkey virus (MPMV) grown in the human NC-37 cell line; (g) the simian sarcoma virus (SSV) grown in the NC-37 cell line; and (h) baboon endogenous virus (BEV) grown in the canine thymus cell line (BKCT). Viruses disrupted by freezing and thawing (10X) were used as absorbants at a concentration of 1 mg. of protein for each ml. containing 50 μg of IgG. The following soluble immunoabsorbants were used at 1 mg/ml for each 50 μg/IgG: (a) mucin from bovine submaxillary gland; (b) hyaluronic acid from human umbilical cord; and (c) actin prepared from human platelets. In addition, gp52 was purified to homogeneity from MMTV (RIII) and MMTV ($C_3H$) via affinity chromatography or guanidinium chloride columns. The purified protein was used at 40 μg for each 50 μg of IgG in 1 ml.

Absorption of the Antisera. Absorption of the primary antibodies, α-MMTV RIII, was achieved by mixing the appropriate absorbant in the indicated amounts, stirring the mixture gently at 37° for 30 minutes and then at 4° for 4 hours. The incubation was then continued without stirring at 4° overnight. Separation of the insoluble immunoabsorbants was achieved by spinning at 8000×g for 15 minutes at 4° twice, using the clear supernatant as the reagent. Soluble immunoabsorbants, including viruses and the purified virus proteins, were separated after incubation by centrifugation at 45,000 rpm in a SW-50.1 rotor for 45 minutes. The high speed supernates were then used as the reagents.

The secondary goat anti-rabbit IgG conjugated to peroxidase was always absorbed with insolubilized human plasma.

Results

It is useful to begin by illustrating positive and negative reactions with representative instances of normal, benign, and malignant samples. Normal breast tissues, whether lactating or not, do not show evidence of a reaction with α-MMTV. Similarly, there is no response seen in the two benign lesions, fibroadenoma and fibrocystic disease. On the other hand, the breast carcinomas, which include an intraductal and invasive type, a metastatic tumor in the ovary, an intraductal, and an invasive tumor, all show clear evidence of a positive reaction.

The specificity of the positive reactions observed was examined by selective absorptions with a variety of solidified and untreated absorbants. After absorption with purified gp52, the α-MMTV is unable to evoke a reaction in the carcinomas. Results of absorptions with other materials are discussed below.

The pattern of staining is quite well exemplified and may be briefly noted. The reaction observed is primarily focal, intracellular and cytoplasmic. Considerable variability was encountered among different tumors, and also among individual cells within a given tumor. The intraductal carcinoma shows considerable staining in the central intraductal lesions, whereas very few cells stain in the intraductal areas located above and below. Likewise, in tumors such as the invasive carcinoma, staining of varying intensity is seen in occasional cells, a situation also observed in the metastatic lesion. In instances where many sections were cut from the same block some levels showed more stained cells than others, and in some instances not all blocks from the same tumor gave a positive reaction.

Table 3 summarizes 131 cases of various types of adenocarcinomas of the breast which were examined by the immunoperoxidase method. Of these, 51 or 39% gave clear evidence of positive reactions. With the possible exception of the 52% positive tumors with intraductal and invasive features, there does not appear to exist any special relationship between the presence of detectable antigens and the histopathologic type of tumor.

TABLE 3

Immunoperoxidase staining of carcinomus of the breast

|  | Cases | Positives | % Positive |
| --- | --- | --- | --- |
| Intraductal | 20 | 0 | 30 |
| Intraductal and Invasive | 31 | 16 | 52 |
| Invasive* | 49 | 19 | 39 |
| Medullary | 12 | 4 | 33 |
| Metastatic+ | 19 | 0 | 32 |
| TOTAL | 131 | 51 | 39 |

*Includes all types of invasive carcinoma (e.g. tubular, lobular, small cell, etc.) except those with predominantly redullary features or associated with intraductal lesions.
+Includes metastases to lymph nodes, lungs, liver adrenal gland and ovaries in proven cases of primary carcinoma of the breast.

As shown by Table 4, none of the 137 normal and benign breast tissues examined showed evidence of a positive reaction. It should be noted that included in this group are 74 cases in which the benign lesions coincided with the presence of malignancy in the same breast.

TABLE 4.

Immunoperoxidase staining of benign and normal breast tissues

|  | Cases | Associated with breast carcinoma | Positives |
| --- | --- | --- | --- |
| Cystic disease* | 81 | 80 | 0 |
| Fribroadenoma | 19 | 4 | 0 |
| Intraductal Papilloma | 10 | 10 | 0 |
| Gynecomastia | 9 | 0 | 0 |
| Resting gland (Normal) | 9 | 0 | 0 |
| Lactating gland (Normal) | 9 | 0 | 0 |
| Total | 137 | 24 | 0 |

*Excluding foci of apocrine metaplasia; absorption studies indicate that in antigen different from the one localized in breast carcinoma is responsible for this reaction.
+in the same breast.

One apparent exception to the absence of reactions in nonmalignant tissues was a positive response observed in foci of apocrine metaplasia, one of the microscopic hallmarks of cystic disease, and in apocrine glands from the axilla and perincum. However, this reaction is apparently different from that observed in malignant cells, since the apocrine cell response is virtually completely removed by absorption of the α-MMTV with mucin, a treatment that does not eliminate the reaction of malignant breast cells.

It was of obvious interest to see whether malignancies other than breast carcinomas contain this antigen, and Table 5 summarizes the results of testing 99 carcinomas from other organs and eight cases of cystosarcoma phyllodes (a primarily mesenchymal breast malignancy). Of these 107 tumors, only one, a mucoepidermoid carcinoma of the parotid gland, gave a positive reaction of uncertain specificity. Two other parotid carcinomas of the same histologic type were negative. It is clear that the antigen being detected by the α-MMTV in human breast carcinomas is confined principally to this neoplastic disease.

TABLE 5

Immunoperoxidase Staining of Malignancies Other Than Breast Carcinomas.

|  | Cases | Positives |
| --- | --- | --- |
| Colon | 12 | 0 |
| Stomach | 3 | 0 |
| Pancreas | 3 | 0 |
| Liver | 4 | 0 |
| Lung | 9 | 0 |
| Endometrium | 22 | 0 |
| Ovary | 20 | 0 |
| Prostate | 8 | 0 |
| Kidney | 5 | 0 |
| Urinary Bladder | 4 | 0 |
| Skin | 2 | 0 |
| Thyroid Gland | 4 | 0 |
| Parotid Gland | 3 | 1 |
| Cystosarcoma Phyllodes | 8 | 0 |
| TOTAL | 107 | 1 |

Primary sites of non-breast carcinomas stained with α-MMTV. Cystosarcoma phyllodes is also listed since it is the most common noncarcinomatous malignancy of the breast.

We have thus far discussed studies which tested the specificity of the reaction by preabsorption of the α-MMTV with gp52. Table 6 summarizes a more extensive examination of this question by pretreatment of the primary antibody with a number of different virus preparations and a variety of antigenic substances that might also be detected by this antibody. The only materials which suppressed the positive reaction of the human breast cancers were the MMTV preparations and the purified pg52 derived from them. It will be noted that RIII and C₃H viruses and the gp52 prepared from both by either affinity chromatography or guanidinium chloride were all equally effective. Further, it did not matter whether the C₃H virus was grown in mouse cells or feline cells. It is evident that the species differences that have been reported for the group-specific antigen of the C₃H and RIII viruses did not affect the reactions being studied here. The fact that C₃H virus grown in feline cells can also block the reaction indicates that the relevant antigen is determined by the virus and not by the cell in which it is grown.

TABLE 6

Absorption Specificity Tests of Immunoperoxidase Staining of Human Breast Carcinomas with α-MMTV.

| Completely Eliminated by: | Not Eliminated by: |
|---|---|
| MMTV (RIII) from milk | RLV, SSV, MPMV and BEV |
| MMTV (C₃H) from MMST | Red Blood Cells (Sheep) |
| MMTV (C₃H) from CrFeK | Normal Plasma (Human) |
| gp52 (RIII) } by Con A affinity | Normal White Blood Cells (Human) |
| gp52 (C₃H) | Collagen (Human) |
| gp52 (RIII) } by guanidium chloride | Actin (Human) |
| gp52 (C₃H) | Mucin (Bovine) |
|  | Hyaluronic acid (Human) |

The absorptions were done using these agents either in the soluble or insolubilized form.

The list of reagents in Table 6 which do not remove the reactivity from α-MMTV serve further to define the specificity of the reaction observed with malignant breast cells. None of the other viruses tested, including RLV, SSV, MPMV, and BEV, contained an antigen sufficiently related to the one in MMTV to block the reaction being observed with breast cancer cells. The same conclusion can be drawn from the negative results obtained with the other materials listed in Table 6. These included sheep red blood cells as a source of heterophile antigens, normal human plasma, white blood cells, milk, normal breast tissue, collagen, actin, mucin, and hyaluronic acid. Finally, the remote possibility that we were observing the carcinoembryonic antigen (CEA) was eliminated by the failure of anti-CEA to stain α-MMTV positive breast tumors under conditions in which CEA is readily found in paraffin sections of colon carcinomas.

The evidence presented above establishes that immunoperoxidase staining of tissue sections can be used to detect a breast cancer antigen which cross reacts with gp52, the group-specific antigen of the mouse mammary tumor virus.

I claim:

1. A method for the detection of breast cancer in a human subject, which method comprises immunologically assaying a sample from said subject for breast cancer specific viral related protein, the assay utilizing the cross-reactivity of the protein with antibodies to Mason-Pfizer Monkey Virus or murine mammary tumor virus.

2. The method of claim 1 wherein plasma samples are taken from said subject before and after initiation of therapy and said assay serves to monitor the effectiveness of said therapy.

3. The method of claim 1 wherein said breast cancer specific viral related protein is human breast cancer DNA polymerase and said sample is a blood plasma sample.

4. The method of claim 3 wherein said DNA polymerase is assayed by radioimmunoassay.

5. The method of claim 4 wherein said radioimmunoassay utilizes human breast cancer DNA polymerase specific antibody and $^{125}$I-human breast cancer DNA polymerase.

6. The method of claim 4 wherein said radioimmunoassay utilizes Mason-Pfizer Monkey Virus or murine mammary tumor virus specific antibody, which are cross-reactive with human breast cancer DNA polymerase, and $^{125}$I-Mason-Pfizer Monkey Virus or $^{125}$I-murine mammary tumor virus, respectively.

7. The method of claim 1 wherein said breast cancer specific viral related protein is viral origin tumor associated protein and said sample is a blood plasma sample.

8. The method of claim 7 wherein said viral origin tumor associated protein is assayed by radioimmunoassay.

9. The method of claim 8 wherein said radioimmunoassay utilizes viral origin tumor associated protein specific antibody and $^{125}$I-viral origin tumor associated protein.

10. The method of claim 8 wherein said radioimmunoassay utilizes Mason-Pfizer Monkey Virus or murine mammary tumor virus specific antibody, wich are cross-reactive with said tumor associated protein, and $^{125}$I-Mason-Pfizer Monkey Virus or $^{125}$I-murine mammary tumor virus, respectively.

11. A method for the immunohistological detection of breast cancer which method comprises treating a human breast tissue section with a first antibody against a virus selected from Mason-Pfizer Monkey Virus and murine mammary tumor virus, thereafter treating said tissue section with a second antibody directed against the first antibody, which second antibody is conjugated to peroxidase enzyme and then treating the resulting tissue section with a substrate of said enzyme which forms a colored precipitate on contact with said enzyme whereby positive staining of said tissue section is indicative of the presence of malignant cells in said tissue.

12. The method of claim 11 wherein said first antibody is murine mammary tumor virus antibody.

13. The method of claim 12 wherein said second antibody is goat anti-rabbit IgG.

14. The method of claim 11 wherein said peroxidase enzyme is horseradish peroxidase enzyme.

* * * * *